US008889917B2

(12) United States Patent
Zeller et al.

(10) Patent No.: US 8,889,917 B2
(45) Date of Patent: Nov. 18, 2014

(54) METHOD OF SUPPLEMENTING THE CATALYST IN CONTINUOUS HYDROFORMYLATION

(71) Applicants: Edgar Zeller, Mannheim (DE); Armin Ulonska, Niederkirchen (DE); Arthur Höhn, Kirchheim (DE); Volker Uhrig, Maxdorf (DE); Rene Magnie, Rödersheim-Gronau (DE); Reimund Fattler, Börrstadt (DE)

(72) Inventors: Edgar Zeller, Mannheim (DE); Armin Ulonska, Niederkirchen (DE); Arthur Höhn, Kirchheim (DE); Volker Uhrig, Maxdorf (DE); Rene Magnie, Rödersheim-Gronau (DE); Reimund Fattler, Börrstadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/860,631

(22) Filed: Apr. 11, 2013

(65) Prior Publication Data
US 2013/0274525 A1 Oct. 17, 2013

Related U.S. Application Data

(60) Provisional application No. 61/623,084, filed on Apr. 12, 2012.

(51) Int. Cl.
*C07C 45/50* (2006.01)

(52) U.S. Cl.
CPC .................... *C07C 45/50* (2013.01)
USPC ......................................................... 568/454

(58) Field of Classification Search
USPC ......................................................... 568/454
See application file for complete search history.

(56) References Cited

U.S. PATENT DOCUMENTS

| 3,527,809 A | 9/1970 | Pruett et al. |
| 4,148,830 A | 4/1979 | Pruett et al. |
| 4,247,468 A | 1/1981 | Cleveland |
| 4,247,486 A | 1/1981 | Brewester et al. |
| 4,668,651 A | 5/1987 | Billig et al. |
| 4,748,261 A | 5/1988 | Billig et al. |
| 4,769,498 A | 9/1988 | Billig et al. |
| 4,774,361 A | 9/1988 | Maher et al. |
| 4,778,929 A | 10/1988 | Zehner et al. |
| 4,835,299 A | 5/1989 | Maher et al. |
| 4,885,401 A | 12/1989 | Billig et al. |
| 5,059,710 A | 10/1991 | Abatjoglou et al. |
| 5,113,022 A | 5/1992 | Abatjoglou et al. |
| 5,179,055 A | 1/1993 | Wink et al. |
| 5,235,113 A | 8/1993 | Sato et al. |
| 5,254,741 A | 10/1993 | Lorz et al. |
| 5,260,491 A | 11/1993 | Wink et al. |
| 5,264,616 A | 11/1993 | Roeper et al. |
| 5,288,918 A | 2/1994 | Maher et al. |
| 5,360,938 A | 11/1994 | Babin et al. |
| 5,391,801 A | 2/1995 | Sato et al. |
| 5,663,403 A | 9/1997 | Sato et al. |
| 5,728,861 A | 3/1998 | Sato et al. |
| 5,728,893 A | 3/1998 | Becker et al. |
| 6,172,267 B1 | 1/2001 | Urata et al. |
| 6,642,420 B1 | 11/2003 | Zehner et al. |
| 6,700,021 B2 | 3/2004 | Bohnen et al. |
| 2006/0004231 A1 | 1/2006 | Zehner et al. |

FOREIGN PATENT DOCUMENTS

| EP | 16286 A2 | 10/1980 |
| EP | 188246 A2 | 7/1986 |
| EP | 0214622 A2 | 3/1987 |
| EP | 423769 A2 | 4/1991 |
| EP | 472 071 A1 | 2/1992 |
| EP | 518 241 A2 | 12/1992 |
| EP | 1114017 A1 | 7/2001 |
| EP | 1231198 A1 | 8/2002 |

*Primary Examiner* — Sikarl Witherspoon
(74) *Attorney, Agent, or Firm* — Drinker Biddle & Reath LLP

(57) ABSTRACT

The present invention relates to a method of supplementing the catalyst in continuous hydroformylation during ongoing operation.

19 Claims, No Drawings

METHOD OF SUPPLEMENTING THE CATALYST IN CONTINUOUS HYDROFORMYLATION

CROSS-REFERENCE TO RELATED APPLICATIONS

This application claims the benefit of U.S. Provisional Application 61/623,084, filed Apr. 12, 2012, which is incorporated herein by reference.

BACKGROUND OF THE INVENTION

The present invention relates to a method of supplementing the catalyst in continuous hydroformylation during ongoing operation.

The continuous hydroformylation of olefins using a rhodium catalyst system is a well-known mature process for the commercial preparation of oxo aldehydes and their hydrogenation products, the oxo alcohols. The process is described in numerous patent documents, e.g. in U.S. Pat. No. 3,527,809, U.S. Pat. No. 4,148,830, U.S. Pat. No. 4,247,486 and U.S. Pat. No. 4,247,468.

In continuous operation, the activity of the catalyst system decreases over the course of time. To maintain the original activity of the catalyst system and the productivity of the reactor system, the catalyst constituents which have become inactive have to be replaced at intervals by addition of fresh transition metal compounds and/or fresh ligands from which further amounts of the active catalyst species are formed under the hydroformylation conditions. Since the hydroformylation is a strongly exothermic reaction, a runaway reaction as a result of the increased catalyst activity has to be avoided at all costs.

At present, when fresh transition metal compounds are added, e.g. in the case of addition of rhodium acetate, the reactor throughput, the amount of starting olefin fed in, the reactor temperature and/or the level of liquid in the reactor is/are reduced before the transition metal compound is added within a short period of time of typically from 2 to 5 hours. This procedure enables the evolution of heat associated with the addition and the temperature increase associated therewith in the reactor to be controlled readily and a runaway reaction to be effectively prevented.

However, this procedure has the disadvantage that the capacity of the hydroformylation plant is not fully utilized during the supplementation of the transition metal compound, which leads to corresponding production losses.

It is an object of the present invention to provide an improved process for preparing saturated $C_3$-$C_{20}$-alcohols from $C_3$-$C_{20}$-aldehydes, in which safe supplementation of the transition metal compound is combined with very low production losses.

It has now surprisingly been found that the transition metal source can be supplemented in continuous hydroformylation without a greatly reduced conversion or a greatly reduced yield having to be accepted when the rate of introduction of the transition metal source into the reaction zone is controlled as a function of the space-time yield. In this way, it is possible, at essentially full loading of the reactor, to keep the activity of the catalyst in the desired target range, with the addition of the transition metal source bringing about only a marginal temperature increase in the reactor which can readily be controlled by engineering means.

SUMMARY OF THE INVENTION

The invention provides a process for continuous hydroformylation, in which an olefin starting material comprising at least one olefin having from 3 to 20 carbon atoms is reacted at elevated temperature and superatmospheric pressure with synthesis gas in the presence of a homogeneous transition metal catalyst complexed with an organophosphorus ligand and free ligand in a reaction zone, where the catalyst is formed in situ in the reaction zone and a solution of a transition metal source is introduced into the reaction zone to compensate catalyst losses, wherein the space-time yield of hydroformylation product in the reaction zone is determined and the rate of introduction of the transition metal source into the reaction zone is controlled as a function of the space-time yield.

A preferred embodiment is a process in which
an adjusting means for setting the rate of introduction of the transition metal source into the reaction zone is provided,
a target value for the space-time yield of hydroformylation product in the reaction zone is set down,
the actual value of the space-time yield is determined,
after a lower limit for the deviation of the actual value from the target value is reached, the amount of transition metal source required for making up the loss of catalyst is determined and
a solution of the transition metal source is introduced into the reaction zone, with the rate of introduction of the transition metal source into the reaction zone being controlled so that the space-time yield does not exceed an upper limit for the deviation of the actual value from the target value.

DESCRIPTION OF THE INVENTION

For the purposes of the invention, the "catalyst losses" refers quite generally to the decrease in the active catalyst in the reaction zone. This can, for example, occur as a result of deactivation, i.e. the formation of transition metal complexes or compounds which are less active or no longer active. This can, for example, also result from the catalyst comprised in the reaction discharge not being able to be recirculated completely to the reaction zone.

"Transition metal source" refers quite generally to transition metals, transition metal compounds and transition metal complexes from which the hydroformylation catalyst is formed in situ in the reaction zone under the hydroformylation conditions. The transition metal source is preferably not preformed catalyst provided outside the reaction zone.

The transition metal is preferably an element of group 9 of the Periodic Table of the Elements and particularly preferably rhodium or cobalt. In particular, rhodium is used as transition metal.

Rhodium compounds or complexes suitable as transition metal source are, for example, rhodium(II) and rhodium(III) salts such as rhodium(II) or rhodium(III) carboxylate, rhodium(II) and rhodium(III) acetate, etc. Furthermore, rhodium complexes such as, dicarbonylrhodium acetylacetonate, diethylenerhodium(I) acetylacetonate, acetylacetonatocyclooctadienylrhodium(I), acetylacetonatonorbornadienylrhodium(I), acetylacetonatocarbonyltriphenylphosphinerhodium(I), etc., are suitable. Preference is given to using rhodium(II) acetate and/or rhodium(III) acetate as transition metal source.

Cobalt compounds suitable as transition metal source are, for example, cobalt(II) sulfate, cobalt(II) carbonate, amine or hydrate complexes thereof, cobalt carboxylates such as cobalt acetate, cobalt ethylhexanoate, cobalt naphthanoate and cobalt caproate. Carbonyl complexes of cobalt, e.g. dicobalt octacarbonyl, tetracobalt dodecacarbonyl and hexacobalt hexadecacarbonyl, are also suitable.

The transition metal compounds and complexes mentioned and further suitable transition metal compounds and complexes are known in principle and are adequately described in the literature, or they can be prepared by a person skilled in the art in a manner analogous to the compounds which are already known.

Particular preference is given to using rhodium(II) and/or rhodium(III) acetate as transition metal source.

In a preferred embodiment of the process of the invention, a solution of the transition metal source in a solvent selected from among water, $C_1$-$C_4$-alkanols and mixtures thereof is introduced into the reaction zone.

In particular, a solution of the transition metal source in water is introduced into the reaction zone. Especially, a solution of rhodium(II) and/or rhodium(III) acetate in water as sole solvent is introduced into the reaction zone.

The concentration of the transition metal source in the solution introduced into the reaction zone is preferably from 0.1 to 10% by weight, particularly preferably from 0.2 to 7.5% by weight, in particular from 0.5 to 5% by weight.

A transition metal complex catalyst which has one or more organophosphorus compound(s) as ligand(s) and is homogeneously soluble in the reaction medium of the hydroformylation reaction is preferably used for the hydroformylation. Preferred ligands are phosphine ligands from the class of triarylphosphines, $C_1$-$C_6$-alkyldiarylphosphines or arylalkyldiphosphines and in particular triphenylphosphine.

Further suitable ligands are diphosphite compounds as are described, for example, in EP 0 214 622 A2, U.S. Pat. No. 4,668,651, U.S. Pat. No. 4,748,261, U.S. Pat. No. 4,769,498, U.S. Pat. No. 4,885,401, U.S. Pat. No. 5,235,113, U.S. Pat. No. 5,391,801, U.S. Pat. No. 5,663,403, U.S. Pat. No. 5,728,861 and U.S. Pat. No. 6,172,267.

Suitable sterically hindered ligands are described, for example, in U.S. Pat. No. 4,774,361, U.S. Pat. No. 4,835,299, U.S. Pat. No. 5,059,710, U.S. Pat. No. 5,113,022, U.S. Pat. No. 5,179,055, U.S. Pat. No. 5,260,491, U.S. Pat. No. 5,264,616, U.S. Pat. No. 5,288,918, U.S. Pat. No. 5,360,938, EP-A 472 071 and EP-A 518 241.

In a particularly preferred embodiment of the process of the invention, a rhodium catalyst comprising triphenylphosphine as ligand is used.

The transition metal concentration in the reaction zone is preferably in the range from 150 to 250 ppm, particularly preferably from 180 to 200 ppm, based on the total liquid content of the reaction zone.

The molar ratio of ligand to transition metal in the reaction zone is preferably in the range from 100:1 to 1000:1, preferably from 200:1 to 500:1, in particular from 300:1 to 500:1.

The gas mixture comprising hydrogen and carbon monoxide which is used is customarily referred to as synthesis gas. The composition of the synthesis gas can vary in a wide range. The molar ratio of carbon monoxide to hydrogen is generally from 2:1 to 1:2, in particular from 45:55 to 50:50.

The hydroformylation can be carried out in a suitable solvent which is inert under the respective reaction conditions. Suitable solvents are, for example, the aldehydes formed in the hydroformylation and higher-boiling reaction components, e.g. the products of aldol condensation. Further suitable solvents are aromatics such as toluene and xylenes, hydrocarbons or mixtures of hydrocarbons, esters of aliphatic carboxylic acids with alkanols, for example Texanol®, and esters of aromatic carboxylic acids, e.g. $C_8$-$C_{13}$-dialkyl phthalates.

Suitable olefin starting materials for the hydroformylation process of the invention are in principle all compounds which comprise one or more ethylenically unsaturated double bonds. These include olefins having terminal and internal double bonds, straight-chain and branched olefins, cyclic olefins and also olefins which have substituents which are essentially inert under the hydroformylation conditions. Preference is given to olefin starting materials comprising olefins having from 2 to 12, particularly preferably from 3 to 8, carbon atoms.

Suitable α-olefins are, for example, ethylene, propene, 1-butene, 1-pentene, 1-hexene, 1-heptene, 1-octene, 1-nonene, 1-decene, 1-undecene, 1-dodecene, etc. Preferred branched internal olefins are $C_4$-$C_{20}$-olefins such as 2-methyl-2-butene, 2-methyl-2-pentene, 3-methyl-2-pentene, internal heptene mixtures, branched, internal octene mixtures, branched, internal nonene mixtures, branched, internal decene mixtures, branched, internal undecene mixtures, branched, internal dodecene mixtures, etc. Further suitable olefins are $C_5$-$C_8$-cycloalkenes such as cyclopentene, cyclohexene, cycloheptene, cyclooctene and derivatives thereof, e.g. their $C_1$-$C_{20}$-alkyl derivatives having from 1 to 5 alkyl substituents. Further suitable olefins are vinylaromatics such as styrene, α-methylstyrene, 4-isobutylstyrene, etc. Further suitable olefins are the esters, monoesters and amides of α,β-ethylenically unsaturated monocarboxylic and/or dicarboxylic acids, e.g. methyl 3-penteneoate, methyl 4-penteneoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., vinyl chloride, allyl chloride, $C_3$-$C_{20}$-alkenols, -alkenediols and -alkadienols, e.g. allyl alcohol, hex-1-en-4-ol, oct-1-en-4-ol, 2,7-octadienol-1. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, vinylcyclohexene, dicyclopentadiene, 1,5,9-cyclooctatriene and butadiene homopolymers and copolymers.

The process of the invention is especially suitable for processes for continuous hydroformylation using an olefin starting material comprising at least one olefin having 3 or 4 carbon atoms. Especially, in the case of these processes, hydroformylation is associated with a considerable evolution of heat on addition of the rhodium source.

In a specific embodiment, an olefin-comprising hydrocarbon mixture which is available industrially is used in the hydroformylation process.

Preference is given to using a propene-comprising hydrocarbon mixture in the process of the invention. A preferred industrial propene-comprising hydrocarbon mixture is the $C_3$ fraction. Propene streams suitable as starting material can comprise not only propene but also propane. The propane content is, for example, from 0.5 to 40% by weight, especially from 1 to 20% by weight, of propane. In a specific embodiment, the propane content is not more than 10% by weight, particularly preferably not more than 6% by weight, based on the total propene-comprising hydrocarbon mixture.

A further preferred industrial olefin mixture is the $C_4$ fraction. $C_4$ fractions can be obtained, for example, by fluid catalytic cracking or steamcracking of gas oil or by steamcracking of naphtha. Depending on the composition of the $C_4$ fraction, a distinction is made between the total $C_4$ fraction (crude $C_4$ fraction), the raffinate I obtained after 1,3-butadiene has been separated off and the raffinate II obtained after isobutene has been separated off. Raffinate II is particularly suitable as olefin-comprising hydrocarbon mixture for the hydroformylation.

The hydroformylation preferably occurs in a reaction zone which can comprise one or more, identical or different reactors. In the simplest case, the reaction zone is formed by a single reactor. The reactors can each have identical or different mixing characteristics. The reactors can, if desired, be divided in one or more places by internals. If two or more reactors form a zone, these can be connected in any desired way, e.g. in parallel or in series. Reactors used can in principle be all reactor types suitable for hydroformylation reactions, for example stirred reactors, bubble column reactors as are described, for example, in U.S. Pat. No. 4,778,929, circulation reactors as are, for example, subject matter of EP-A 1 114 017, tube reactors, with the individual reactors being able to have a series of different mixing characteristics, as described, for example, in EP-A 423 769; furthermore, it is possible to use compartmented reactors as are, for example, subject matter of EP-A 1 231 198 or U.S. Pat. No. 5,728,893.

The temperature in the reaction zone is generally in the range from about 50 to 200° C., preferably from about 60 to 180° C., in particular from about 70 to 160° C. The reaction is preferably carried out at a pressure in the range from about 10 to 700 bar, preferably from 15 to 200 bar, in particular from 15 to 60 bar.

The space-time yield is preferably determined by measuring the aldehyde content in the discharge from the reaction zone. This measurement is preferably carried out by means of an on-line measurement device. However, it is also possible to take samples from the discharge from the reaction zone at regular intervals and determine the aldehyde content in a separate analysis apparatus. The aldehyde content can be determined, for example, by gas chromatography, infrared spectroscopy, colorimetry or chemiluminescence analysis. In the quantitative chemiluminescence analysis, it is thus possible, for example, to determine the aldehyde content with high accuracy after conversion of the aldehyde into a fluorescent derivative, e.g. using Fluoral-P (4-amino-3-penten-2-one).

In the simplest case of the process of the invention, the rate of introduction of the transition metal source into the reaction zone is determined as a function of the space-time yield (STY) by means of a suitable adjusting means (actuator).

In the simplest case of the process of the invention, back-coupling of the output parameter (STY) to the rate of introduction in the sense of regulation can be dispensed with. Thus, for example, after a lower limit for the space-time yield in the reaction zone is reached, a solution of the transition metal source can be introduced so that the resulting increase in the transition metal concentration in the reactor does not exceed a predetermined limit. In this way, a runaway reaction is generally reliably avoided.

The transition metal concentration in the reaction zone is preferably in the range from 150 to 250 ppm, particularly preferably from 180 to 200 ppm, based on the total liquid content of the reaction zone. The transition metal is especially rhodium. Here, the transition metal concentration relates only to the amount of "active" transition metal, i.e. transition metal in catalytically active form or a form which can be converted into this under the reaction conditions.

The rate of introduction of the transition metal source into the reaction zone is preferably in the range from 0.1 ppm to 10 ppm of transition metal source per day, particularly preferably in the range from 0.5 ppm to 5 ppm of transition metal source per day, based on the total liquid content of the reaction zone. This applies both to the control variant and the regulated variant of the process of the invention. The transition metal is especially rhodium. The transition metal source is especially rhodium acetate.

The temperature increase in the reaction zone brought about by the introduction of the rhodium source is preferably less than 2 K, preferably less than 1 K, in particular less than 0.5 K. This applies both to the controlled variant and the regulated variant of the process of the invention.

Suitable devices for controlling the rate of introduction of the transition metal source into the reaction zone are selected from among flow limiters, metering valves and metering pumps. In a suitable embodiment, a combination of at least one pump and at least one flow limiter and/or at least one metering valve is used for controlling the rate of introduction. In a preferred embodiment, at least one metering pump is used for controlling the rate of introduction of the transition metal source into the reaction zone. The metering pump simultaneously takes on the functions of all system components which are otherwise necessary, e.g. pump, metering valve, optionally shutoff valve, etc. Suitable metering pumps are known to those skilled in the art and have the task of transporting accurate amounts of liquid. Such pumps can be, for example, diaphragm pumps or piston pumps.

In a preferred embodiment, the process of the invention comprises a device for regulating the rate of introduction of the transition metal source into the reaction zone as a function of the respective actual value of the STY, as described above. The abovementioned devices for controlling the rate of introduction are suitable adjusting means (actuators) in the case of a regulated embodiment of the process of the invention. Then, they convert, for example, the electronic signals (e.g. commands from the control computer) into an appropriate mechanical increase or reduction in the inflow rate of the solution of the transition metal source into the reaction zone and thus exert a regulating effect in the regulating system used according to the invention.

The lower limit to the deviation of the actual value of the space-time yield from the target value is preferably not more than 40%, particularly preferably not more than 30%, based on the target value.

The upper limit to the deviation of the actual value of the space-time yield from the target value is preferably not more than 10%, particularly preferably not more than 5%, based on the target value.

The separation of the hydroformylation product from the discharge from the reaction zone can be carried out in various ways. It is possible, for example, to use a hydroformylation process with liquid discharge, as is described, for example, in U.S. Pat. No. 4,148,830, EP-A 16 286, EP-A 188 246 or EP-A 423 769. Preference is given to a liquid discharge process in which the essentially liquid, except for the synthesis gas used in excess for the hydroformylation, discharged from the reaction zone is depressurized, and, as a result of the reduction in pressure, the discharge is separated into a liquid phase which consists essentially of high-boiling by-products, the homogeneously dissolved hydroformylation catalyst, part of the hydroformylation product and dissolved, unreacted propylene and propane and a gas phase which consists essentially of hydroformylation product, unreacted propylene and propane and also unreacted carbon monoxide and hydrogen and also inerts (e.g. $N_2$, $CO_2$, methane). The liquid phase can, optionally after further removal of product aldehydes comprised therein, be fed as recycle stream back into the reactor. The crude hydroformylation product is obtained by at least partial condensation of the gas phase. The gas phase remaining after the condensation is completely or partly recirculated to the reaction zone. The gas and liquid phases initially obtained in the depressurization stage can advantageously be worked up by the process described in WO 97/07086. For this purpose, the liquid phase is heated and introduced into the upper region of a column, while the gas phase is introduced into the bottom of the column. Liquid phase and gas phase are thus conveyed in countercurrent. As a result of the intimate contact of the gas phase with the liquid phase, the residual amounts of hydroformylation product, unreacted propylene and propane present in the liquid phase are transferred into the gas phase, so that the gas stream leaving the top of the column is enriched in hydroformylation product and also unreacted propene and propane compared to the gas stream introduced at the lower end of the column.

When a liquid discharge is taken from the reaction zone, the target value for the space-time yield of hydroformylation product in the reaction zone is preferably from 75 to 120 kg/m$^3$h, particularly preferably from 85 to 110 kg/m$^3$h, in particular from 94 to 100 kg/m$^3$h.

As an alternative, it is possible to employ the gas recycle process in which a gas stream is taken off from the gas space of the hydroformylation reactor. This gas stream consists essentially of synthesis gas, unreacted propylene and propane, with, depending on the vapor pressure in the hydroformylation reactor, the hydroformylation product formed in the hydroformylation reaction being entrained. The entrained crude hydroformylation product is condensed out from the gas stream, e.g. by cooling, and the gas stream which has been freed of the liquid fraction is recirculated to the hydroformylation reactor. The unreacted propylene and propane comprised in solution in the condensed-out crude hydroformylation product can then, as described, be liberated in, for example, a degassing column.

When a gaseous discharge is taken from the reaction zone, the target value for the space-time yield of hydroformylation product in the reaction zone is preferably from 50 to 75 kg/m$^3$h, particularly preferably from 55 to 70 kg/m$^3$h, in particular from 60 to 65 kg/m$^3$h.

The invention is illustrated by the following, nonlimiting examples.

EXAMPLES

Example 1

Comparative Example Using Conventional Rhodium Supplementation

The reactor of a running process for the hydroformylation of propylene using a rhodium-triphenylphosphine-carbonyl complex as catalyst and gaseous reaction discharge was supplied with fresh rhodium acetate after the space-time yield had dropped to a value of about 45 kg/m$^3$h. For this purpose, the plant loading (propylene throughput) was reduced beforehand from 100% to about 60%, the propylene content in the recycle gas was reduced from about 40% by volume to about 30% by volume, the liquid level in the reactor was reduced by about 30% and the reactor temperature was reduced from 109° C. to 105° C. before 50 l of a 5% strength by weight aqueous rhodium acetate solution were introduced over a period of about 2 hours by means of a pump. A temperature increase of up to 4° C. was observed, and this could easily be regulated by means of heat removal opportunities present. The plant loading was then brought back to 100% and the operating conditions were adapted accordingly. The lower temperature (107° C. instead of 109° C.) necessary for full loading reflected a higher activity of the catalyst after supplementation. The entire rhodium supplementation process took about 18 hours.

Example 2

Continuous Rhodium Introduction According to the Invention

A reactor operated at full load in a continuously operated process for the hydroformylation of propylene using a rhodium-triphenylphosphine-carbonyl complex as catalyst and gaseous reaction discharge was supplied with 100 l of a 2.5% by weight aqueous rhodium acetate solution by means of a metering pump over a period of 10 days after the space-time yield had dropped to a value of about 45 kg/m$^3$h. No appreciable temperature increase in the reactor was observed over the introduction time. The reactor temperature required for full load could be reduced by about 1° C. after rhodium supplementation, which indicates an increase in the catalyst activity. After the end of the addition of the rhodium acetate, the space-time yield was back at a desired value of from 60 to 65 kg/m$^3$h.

The invention claimed is:

1. A process for continuous hydroformylation, in which an olefin starting material comprising at least one olefin having from 3 to 20 carbon atoms is reacted at elevated temperature and superatmospheric pressure with synthesis gas in the presence of a homogeneous transition metal catalyst complexed with an organophosphorus ligand and free ligand in a reaction zone, where the catalyst is formed in situ in the reaction zone and a solution of a transition metal source is introduced into the reaction zone to compensate catalyst losses, wherein the space-time yield of hydroformylation product in the reaction zone is determined and the rate of introduction of the transition metal source into the reaction zone is controlled as a function of the space-time yield.

2. The process according to claim 1, wherein
an adjusting means for setting the rate of introduction of the transition metal source into the reaction zone is provided,
a target value for the space-time yield of hydroformylation product in the reaction zone is set down,
the actual value of the space-time yield is determined,
after a lower limit for the deviation of the actual value from the target value is reached, the amount of transition metal source required for making up the loss of catalyst is determined and
a solution of the transition metal source is introduced into the reaction zone, with the rate of introduction of the transition metal source into the reaction zone being controlled so that the space-time yield does not exceed an upper limit for the deviation of the actual value from the target value.

3. The process according to claim 2, wherein the lower limit to the deviation of the actual value of the space-time yield from the target value is not more than 40%, based on the target value.

4. The process according to claim 2, wherein the upper limit to the deviation of the actual value of the space-time yield from the target value is not more than 10%, based on the target value.

5. The process according to claim 1, wherein the transition metal concentration in the reaction zone is in the range from 150 to 250 ppm, based on the total liquid content of the reaction zone.

6. The process according to claim 1, wherein the rate of introduction of the transition metal source into the reaction zone is in the range from 0.1 ppm to 10 ppm of transition metal source per day, based on the total liquid content of the reaction zone.

7. The process according to claim 1, wherein the temperature increase in the reaction zone brought about by the introduction of the transition metal source is less than 2 K.

8. The process according to claim 1, wherein rhodium is used as transition metal.

9. The process according to claim 1, wherein rhodium(II) acetate and/or rhodium(III) acetate is used as transition metal source.

10. The process according to claim 1, wherein a solution of the transition metal source in a solvent selected from among water, $C_1$-$C_4$-alkanols and mixtures thereof is introduced into the reaction zone.

11. The process according to claim 1, wherein the concentration of the transition metal source in the solution introduced into the reaction zone is from 0.1 to 10% by weight.

12. The process according to claim 1, wherein the ligand is selected from among triarylphosphines, $C_1$-$C_6$-alkyldiarylphosphines and arylalkyldiphosphines.

13. The process according to claim 1, wherein a rhodium catalyst comprising triphenylphosphine as ligand is used.

14. The process according to claim 1, wherein the molar ratio of ligand to transition metal in the reaction zone is in the range from 100:1 to 1000:1.

15. The process according to claim 1, wherein a propene-comprising hydrocarbon mixture is used for the hydroformylation.

16. The process according to claim 1, wherein a liquid discharge is taken off from the reaction zone to separate off the hydroformylation product.

17. The process according to claim 16, wherein the target value for the space-time yield of hydroformylation product in the reaction zone is from 75 to 120 kg/m$^3$h.

18. The process according to claim 1, wherein a gaseous discharge is taken off from the reaction zone to separate off the hydroformylation product.

19. The process according to claim 18, wherein the target value for the space-time yield of hydroformylation product in the reaction zone is from 50 to 75 kg/m$^3$h.

* * * * *